US00PP35793P3

(12) United States Plant Patent
Scheffers

(10) Patent No.: US PP35,793 P3
(45) Date of Patent: May 7, 2024

(54) ***CEROPEGIA* PLANT NAMED 'MEREL'**

(50) Latin Name: ***Ceropegia linearis* E. Mey. subsp. *woodii* (Schltr.) H. Huber syn. *Ceropegia woodii.***
Varietal Denomination: Merel

(71) Applicant: Aad Scheffers, Honselersdijk (NL)

(72) Inventor: Aad Scheffers, Honselersdijk (NL)

( * ) Notice: Subject to any disclaimer, the term of this patent is extended or adjusted under 35 U.S.C. 154(b) by 0 days.

(21) Appl. No.: 18/445,242

(22) Filed: Jun. 13, 2023

(65) Prior Publication Data

US 2023/0403959 P1 Dec. 14, 2023

(30) Foreign Application Priority Data

Jun. 13, 2022 (QZ) ..... PBR 2022/1479

(51) Int. Cl.
*A01H 5/02* (2018.01)
*A01H 6/00* (2018.01)
*A01H 6/08* (2018.01)

(52) U.S. Cl.
USPC ..... Plt./226
CPC ..... *A01H 6/08* (2018.05); *A01H 6/00* (2018.05)

(58) Field of Classification Search
USPC ..... Plt./226
CPC ..... A01H 5/02; A01H 5/00
See application file for complete search history.

*Primary Examiner* — Kent L Bell
(74) *Attorney, Agent, or Firm* — Samuel R. McCoy, Jr.

(57) ABSTRACT

A new and distinct *Ceropegia woodii* plant named 'Merel' which is characterized by a trailing habit, small narrowly cordate to near-deltoid foliage, conspicuously variegated foliage that is broadly margined white, a moderately fast rate of growth, as well as the stability of these characteristics from generation to generation.

3 Drawing Sheets

Latin name of the genus and species: The Latin name of the genus and species of the novel variety disclosed herein is *Ceropegia linearis* E. Mey. subsp. *woodii* (Schltr.) H. Huber syn. *Ceropegia woodi.*

Variety denomination: The inventive variety of *Ceropegia* disclosed herein has been given the variety denomination 'Merel'.

CROSS REFERENCE TO RELATED APPLICATIONS

This application claims priority to the Community Plant Variety Rights application number 2022/1479, filed Jun. 13, 2022, which is herein incorporated by reference.

BACKGROUND OF THE INVENTION

Parentage: The new plant originated as a spontaneous, partial-plant, branch mutation. The branch mutation was discovered at a greenhouse in Honselersdijk, The Netherlands, in March of 2020, growing amongst a plurality of cultivated *Ceropegia woodii* 'Green Love' (not patented) plants. The mutation exhibited conspicuously variegated foliage and improved vigor, relative to the parent. From said mutated branch, a plurality of cuttings was harvested, rooted, and grown to a mature size in order to evaluate stability and uniqueness of the characteristics first observed. Of these new plants, most exhibited at least some degree of reversion in the foliage color, back to that of the parental phenotype. All plants that showed reversion were discarded, while stem cuttings were harvested from those plants that retained the unique variegation. This process was repeated several times until all progeny from an individual cutting-grown plant retained the characteristics first observed in March of 2020. This specific ortet was selected for commercialization and given the name, 'Merel'.

Asexual Reproduction: Asexual reproduction of the new cultivar 'Merel', by way of softwood stem cuttings, was first initiated in March of 2022 in Honselersdijk, The Netherlands. Through more than 6 subsequent generations, the unique features of this cultivar have proven to be stable and true to type.

SUMMARY OF THE INVENTION

The cultivar 'Merel' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Merel'. These characteristics in combination distinguish 'Merel' as a new and distinct *Ceropegia* cultivar:

1. *Ceropegia* 'Merel' exhibits relatively small, narrowly cordate to near-deltoid foliage; and
2. *Ceropegia* 'Merel' exhibits prominently variegated foliage that is green with the veins and areas of the laminar surface immediately adjacent to veins colored with a light greyed-green; and
3. *Ceropegia* 'Merel' exhibits foliage that is broadly margined with white margins; and
3. *Ceropegia* 'Merel' exhibits a fast growth rate.

BOTANICAL DESCRIPTION OF THE PLANT

Figure 1:
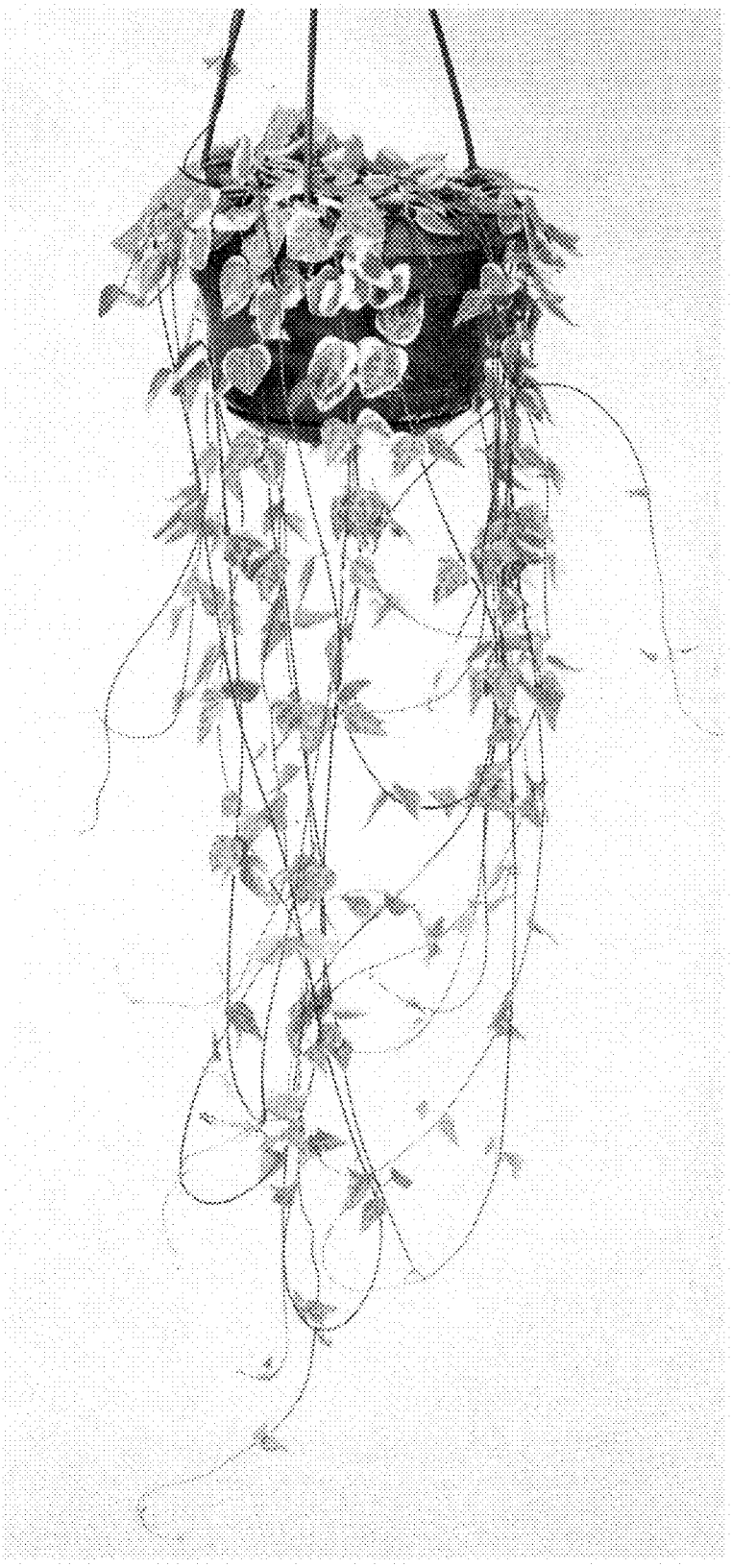
FIG. 1 illustrates, as nearly true as it is reasonably possible to make the same in color photographs of this type, an exemplary 5-month-old 'Merel' plant in a 14 cm nursery pot, grown in a greenhouse in Honselersdijk, The Netherlands.
Figure 2:
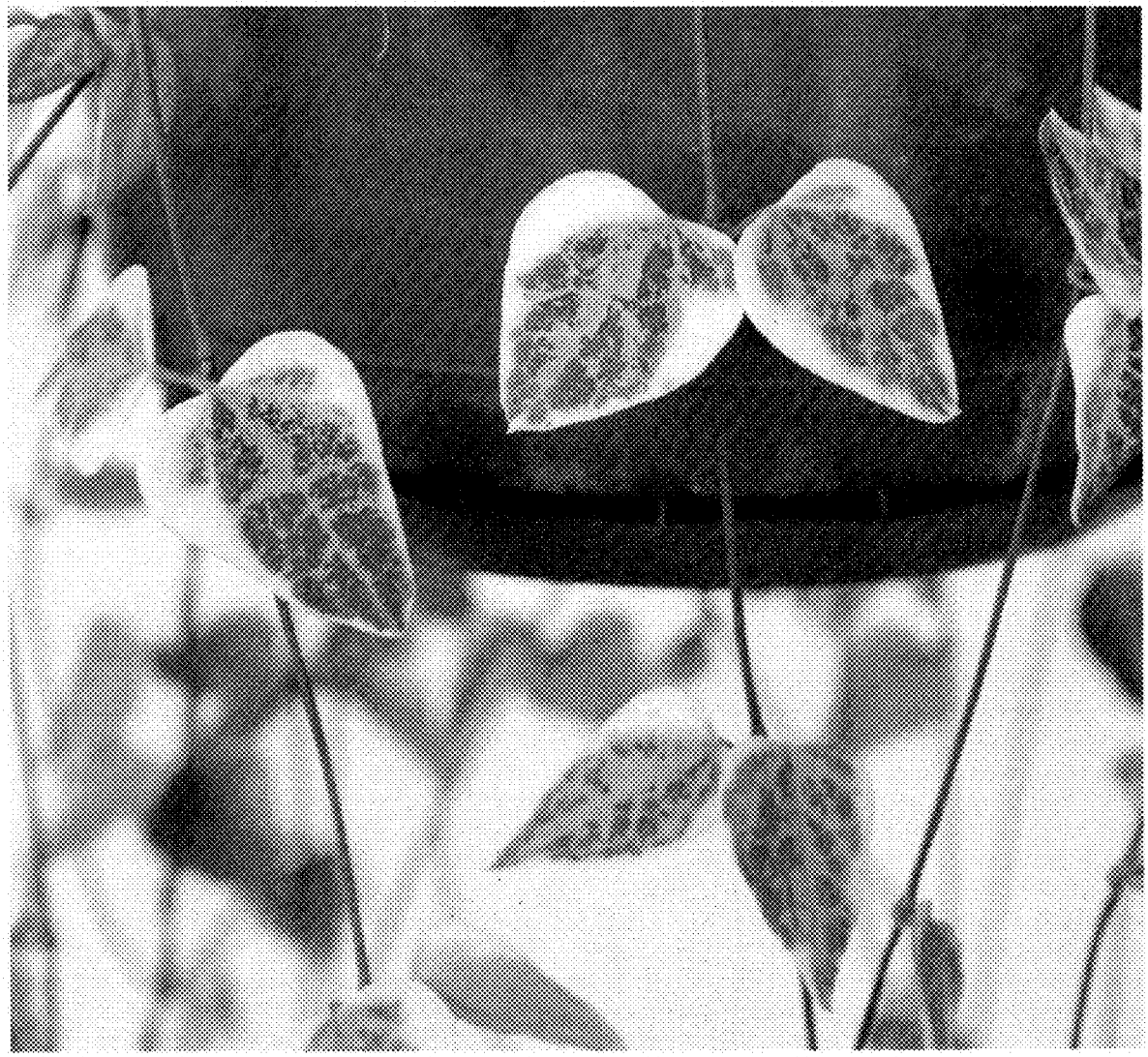
FIG. 2 illustrates, as nearly true as it is reasonably possible to make the same in color photographs of this type, the mature foliage of 'Merel'.
Figure 3:
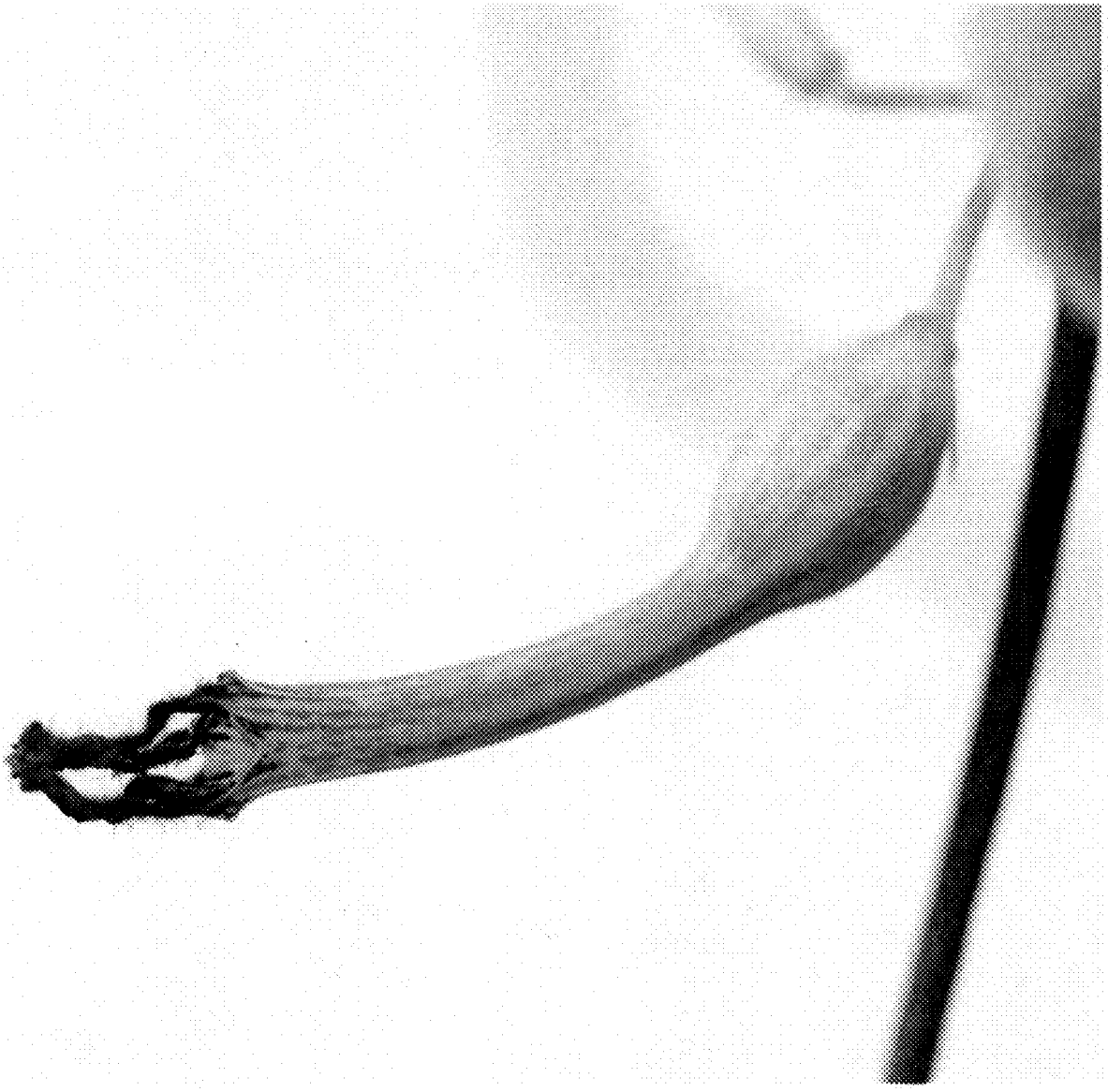
FIG. 3 illustrates, as nearly true as it is reasonably possible to make the same in color photographs of this type, the flower of 'Merel'.

The following observations and measurements were made in August of 2022 and describe a 5-month-old 'Merel' plant grown in a 14 cm nursery pot grown in a greenhouse in Honselersdijk, The Netherlands. Plants were grown using conventional greenhouse production protocols for *Ceropegia* which consisted of growing under 50 percent shade with regular overhead irrigation and fertilizer applications as needed. Pesticides were used to control thrips, but no pest or disease control measures were otherwise utilized in production. No photoperiodic treatments or artificial light was given to the plants.

Those skilled in the art will appreciate that certain characteristics will vary with older or, conversely, with younger plants. 'Merel' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2015 (sixth edition).

A botanical description of 'Merel' and comparisons with the parent and most similar commercial variety of *Ceropegia* are provided below.

Plant description:

*Growth habit.*—Evergreen trailing vine perennial.

*Average height from base to top of foliage.*—In a hanging basket, the plant is 97.0 cm from the top of the floral plane to the apex of the lowest trailing stem.

*Average width.*—21.5 cm.

*Growth rate.*—Moderately fast growing.

*Plant vigor.*—Highly vigorous.

*Propagation method.*—Softwood stem cuttings; rooting is initiated in approximately 14 days, when grown in a greenhouse with an ambient average temperature of 20 degrees Celsius.

*Time to produce a finished plant.*—Approximately 5 months is required to produce a fully rooted and marketable 14 cm plant when grown under greenhouse conditions.

*Disease and pest resistance or susceptibility.*—Plants have not been observed to be susceptible or resistant to pathogens and pests common to *Ceropegia woodii*.

*Environmental tolerances.*—Adapt to at least USDA Zones 8 and 12; moderate tolerance to rain; high tolerance to wind; moderate tolerance to drought.

Root system:

*General.*—Caudices at the base of main stems, at and slightly below the soil level, give rise to a moderately dense network of fleshy roots.

*Distribution in the soil profile.*—Roots are relatively shallow.

*Texture.*—Fleshy; no root hairs present.

Stem:

*Branching habit.*—Basally branching main stem; freely branching with lateral branches.

*Number of main stems per plant.*—15.

*Number of lateral branches per plant.*—10.

*Aspect.*—Rounded.

*Length of main stems.*—67.8 cm.

*Diameter of main stems.*—0.125 cm at the widest point.

*Internode length on main stems.*—7.0 cm.

*Attitude.*—Prostrate; weeping, when grown in a hanging basket.

*Strength.*—Moderately strong.

*Texture and luster*—Glabrous and matte.

*Color, juvenile.*—Yellow-green, nearest to RHS 152A, and finely blotched with a lighter shade of yellow-green, nearest to RHS 147D.

*Color, mature.*—Yellow-green, nearest to RHS 148B, and finely blotched with a lighter shade of yellow-green, nearest to RHS 147D.

*Color at internodes.*—Yellow-green, nearest to RHS 148B, and finely blotched with a lighter shade of yellow-green, nearest to RHS 147D; suffused with greyed-purple, nearest to RHS N186C.

Foliage:

*Arrangement.*—Opposite.

*Division.*—Simple.

*Attachment.*—Petiolate.

*Quantity.*—Average of 20 leaves per lateral branch.

*Lamina.*—Dimensions — 2.3 cm long and 1.9 cm wide, on average. Shape — Narrow cordate to near deltoid. Aspect — Flat. Apex — Acute. Base — Cordate to shallowly truncate. Margin — Entire; not undulated. Pubescence, texture and luster of adaxial surface — Glabrous, smooth, and matte. Pubescence, texture and luster of abaxial surface — Glabrous, smooth, and matte. Color — Juvenile foliage, adaxial surface — Yellow-green, nearest to RHS 146C; blotched greyed-green, nearest to RHS 192A; veins are greyed-green, nearest to RHS 192A; irregularly and narrowly margined white, nearest to RHS 155A. Juvenile foliage, abaxial surface — Yellow-green, nearest to RHS 148D; irregularly and narrowly margined white, nearest to a mixture of RHS 155A and N155B. Mature foliage, adaxial surface — Green, nearest to a combination of RHS 137C and NN137A; veins and areas of the laminar surface immediately adjacent to veins is greyed-green, nearest to RHS 188C; irregularly and broadly margined white, nearest to RHS 155C. Mature foliage, abaxial surface — Greyed-green, nearest to RHS 191C; often but not always suffused with greyed-purple, nearest to RHS N187C; irregularly and broadly margined white, nearest to RHS 155C. Venation — Pattern — Pinnate. Venation color, adaxial surface — Greyed-green, nearest to RHS 188C. Venation color, abaxial surface — Yellow-green, nearest to RHS 147B.

*Petiole.*—Length — 0.5 cm. Width — 0.1 cm. Texture — Smooth and glabrous. Luster — Matte.

Strength — Moderately strong. Color, adaxial surface — Greyed-red, nearest to RHS 182D. Color, abaxial surface — Greyed-red, nearest to RHS 182D.

Inflorescence:

*Inflorescence type.*—Cyme.

*Natural flowering season.*—Late June through early August in Honselersdijk, the Netherlands.

*Dimensions.*—Approximately 3.3 cm long, including peduncle, and 6.0 cm wide.

*Quantity of open flowers and buds per inflorescence.*—4.

*Attitude.*—Pendulous.

*Peduncles.*—Length — Average of 1.1 cm. Diameter — Average of 0.6 cm. Attitude — Outward, at an approximate angle of 30 degrees from horizontal. Strength — Moderately strong. Texture and luster — Smooth, glabrous and matte. Color — Greyed-green, nearest to RHS 197B.

Bud:

*Shape.*—Narrowly oblong.

*Dimensions.*—7.0 mm long and 1.5 mm in diameter.

*Color.*—Immature sepals and corolla tube are yellow-green, nearest to RHS 150D; immature petals are greyed-orange, nearest to RHS N170D.

*Texture.*—Smooth and glabrous.

*Luster.*—Slightly glossy.

Flower:

*Form.*—Tubulate; the corolla is fused into a floral tube, swollen at the base, with free petal lobes, distally, which are fused at their apices.

*Attitude.*—Outward to upright.

*Lastingness.*—Approximately 14 days.

*Persistence.*—Not persistent; self-cleaning.

*Fragrance.*—Not fragrant.

*Flower depth.*—2.3 cm.

*Flower diameter.*—0.4 cm.

*Diameter of floral throat.*—0.3 cm.

*Floral throat texture.*—Glabrous; smooth.

*Diameter of floral tube.*—0.3 cm at the distal end; at the base, where the floral tube is swollen, the diameter is 0.4 cm.

*Length of floral tube.*—1.7 cm.

*Floral tube texture.*—Glabrous; smooth.

*Pedicels.*—Attitude — Outward, at an average angle of 25 degrees to the peduncle; varying from 10 to 60 degrees. Dimensions — 6.0 mm long and 0.5 mm in diameter. Strength — Moderately strong. Texture and luster — Smooth, glabrous, and matte. Color — Greyed-green, nearest to RHS 197C.

*Petals.*—Quantity of Petals — 5. Arrangement — The petals are fused into a long floral tube, with a single whorl of free petal lobes, distally. Attitude of petal lobes — Curved inward, particularly at and near the apex, and fused to all other petal lobes at the apex, forming a "cage" over the floral throat. Shape of petal lobes — Narrowly spatulate. Aspect of petal lobes — Strongly carinate and irregularly twisted. Dimensions, free portion of petals — 0.6 cm long and 0.2 cm wide. Apex — Near-obtuse yet appearing as near-acute used. Base — Truncate; fused at the base. Margin — Entire and ciliate; hairs are 0.3 mm in length and are colored with a mixture of greyed-purple and black, nearest to RHS N186A and 202A. Petal lobes are not undulated. Pubescence, texture and luster of outer surface — Smooth, glabrous, and slightly glossy. Pubescence, texture and luster of inner surface — Smooth, glabrous and matte. Corolla tube color when opening, inner surface — Swollen portion of the floral tube near the base of the corolla is greyed-purple, nearest to RHS 186B; narrower portion of the floral tube is purple, nearest to RHS N77A. No visible venation. Corolla tube color when opening, outer surface — Swollen portion of the floral tube near the base of the corolla is greyed-green, nearest to a combination of RHS 198C and 198D; narrower portion of the floral tube is a mixture of purple and greyed-red, nearest to RHS 75C and 182D. No visible venation. Petal lobe color when opening, inner surface — Nearest to a mixture of greyed-purple and black, RHS N186A and 202A. No visible venation. Petal lobe color when opening, outer surface — Nearest to a mixture of greyed-purple and black, RHS N186A and 202A. No visible venation. Corolla tube color when fully open, inner surface — Swollen portion of the floral tube near the base of the corolla is greyed-green, nearest to a combination of RHS 198C and 198D; narrower portion of the floral tube is a mixture of purple and greyed-red, nearest to RHS 75C and 182D. No visible venation. Corolla tube color when fully open, outer surface — Swollen portion of the floral tube near the base of the corolla is greyed-purple, nearest to RHS 186B; narrower portion of the floral tube is purple, nearest to RHS N77A. No visible venation. Petal lobe color when fully opened, inner surface — Greyed-purple, nearest to RHS N186A. No visible venation. Petal lobe color when fully opened, outer surface — Greyed-purple, nearest to RHS N186A. No visible venation. Floral throat color — Nearest to a mixture of purple and greyed-red, RHS 75C and 182D. No visible venation. Corolla tube color when faded, inner surface — Colors do not fade. No visible venation. Corolla tube color when faded, outer surface — Swollen portion of the floral tube near the base of the corolla is greyed-green, nearest to RHS 198D; narrower portion of the floral tube is greyed-red, nearest to RHS 182D yet lighter. No visible venation. Petal lobe color when faded, inner surface — Nearest to a mixture of greyed-purple and black, RHS N186A and 202A. No visible venation. Petal lobe color when faded, outer surface — Nearest to a mixture of greyed-purple and black, RHS N186A and 202A. No visible venation.

*Calyx.*—Shape — Rotate; single whorl of sepals. Dimensions —0.4 cm in diameter and 0.2 cm deep. Sepals — Arrangement — Sepals are rotate and fused at the base. Quantity — 5. Shape — Linear. Dimensions — 2.0 mm long and 0.4 mm wide. Apex — Narrow acuminate. Base — Cuneate; fused. Margin — Entire; not undulated. Pubescence, texture and luster, upper surface — Smooth; glabrous; matte. Pubescence, texture and luster, lower surface — Smooth; glabrous; matte. Color when opening, inner surface — White, nearest to RHS N155B. Color when opening, outer surface — White, nearest to RHS N155B. Color when fully opened, inner surface — White, nearest to RHS N155B. Color when fully opened, outer surface — White, nearest to RHS N155B.

Reproductive organs:

*General description.*—Stamens and pistils are adnated into a gynostegium.

*Dimensions.*—Approximately 1.2 mm long and 1.0 mm wide.

*Color.*—Reduced filaments are a combination of white and greyed-yellow, nearest to RHS N155A, 160C, and 160D; reduced anthers are greyed-orange, nearest to RHS 164A; reduced pistils are white, nearest to RHS N155A.

*Pollen, amount.*—Pollen is sparse and massed into globular pollinia at the base of the gynostegium.

*Pollinia color.*—Greyed-orange, nearest to RHS 164A.

*Ovary color.*—Greyed-purple, nearest to RHS N186B.

Seed and Fruit: To date, seeds and fruit have not been observed.

Comparisons with the parent plant: Plants of the new cultivar 'Merel' differ from *Ceropegia woodii* 'Green Love' (not patented) parent by the characteristics described in Table 1.

TABLE 1

| Characteristic | 'Merel' | 'Green Love' |
|---|---|---|
| Rate of growth. | Faster-growing than 'Green Love'. | Slower-growing than 'Merel'. |
| Expression of foliage variegation. | Adaxial foliar surface is green and strongly colored with greyed-green along the veins and areas of the laminar surface adjacent to veins. | Adaxial foliar surface is green with light greyed-green mottling. |

Comparison with the most similar *Ceropegia* cultivar known to the inventor: Plants of the new cultivar 'Merel' differ from the commercial variety, *Ceropegia* 'Variegata' (not patented), in the following characteristics described in Table 2 below.

TABLE 2

| Characteristic | 'Merel' | 'Variegata' |
|---|---|---|
| Rate of growth. | Faster-growing than 'Variegata'. | Slower-growing than 'Merel'. |
| Foliage shape. | Narrow cordate to near deltoid. | Broadly cordate to nearly-round. |
| Foliage size. | Smaller than 'Variegata'. | Larger than 'Merel'. |
| Presence of foliage variegation. | Adaxial foliar surface is green and strongly colored with greyed-green along the veins and areas of the laminar surface adjacent to veins. | Adaxial foliar surface is green with light greyed-green mottling and often suffused with red-purple. |

That which is claimed is:

1. A new and distinct *Ceropegia woodii* plant named 'Merel', substantially as described and illustrated herein.

* * * * *